United States Patent
St. Martin et al.

(10) Patent No.: US 8,052,703 B2
(45) Date of Patent: Nov. 8, 2011

(54) MEDICAL DEVICES WITH CUTTING ELEMENTS

(75) Inventors: Timothy R. St. Martin, Vista, CA (US); Randall O. Wallingford, Fallbrook, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

(21) Appl. No.: 11/169,415

(22) Filed: Jun. 29, 2005

(65) Prior Publication Data

US 2007/0016232 A1    Jan. 18, 2007

(51) Int. Cl.
*A61B 17/22* (2006.01)
*A61B 17/32* (2006.01)
*A61D 1/02* (2006.01)
*A61M 29/00* (2006.01)

(52) U.S. Cl. .................. 606/159; 606/170; 606/194

(58) Field of Classification Search .......... 600/564, 600/572, 562; 606/159, 170, 191, 192, 194; 604/96

See application file for complete search history.

(56) References Cited

U.S. PATENT DOCUMENTS

| | | | |
|---|---|---|---|
| 5,152,774 A * | 10/1992 | Schroeder | 428/457 |
| 5,195,969 A | 3/1993 | Wang et al. | |
| 5,196,024 A | 3/1993 | Barath | |
| 5,209,799 A | 5/1993 | Vigil | |
| 5,270,086 A | 12/1993 | Hamlin | |
| 5,336,234 A | 8/1994 | Vigil et al. | |
| 5,797,877 A | 8/1998 | Hamilton et al. | |
| 6,394,964 B1 * | 5/2002 | Sievert et al. | 600/564 |
| 2002/0165523 A1 | 11/2002 | Chin et al. | |
| 2003/0163148 A1 | 8/2003 | Wang et al. | |
| 2003/0163157 A1 | 8/2003 | McMorrow et al. | |
| 2003/0229370 A1 | 12/2003 | Miller | |
| 2004/0019362 A1 * | 1/2004 | Ferrera et al. | 606/192 |
| 2005/0089438 A1 | 4/2005 | Stinson | |
| 2005/0149102 A1 | 7/2005 | Radisch, Jr. et al. | |
| 2006/0106413 A1 * | 5/2006 | Bence et al. | 606/192 |
| 2007/0274855 A1 * | 11/2007 | Nilsson et al. | 420/38 |

FOREIGN PATENT DOCUMENTS

JP    11293405    * 10/1999

OTHER PUBLICATIONS http://waybackmachine.org/20030701000000/http://www.stal.com.cn/pdffile/410420425440a.pdf(Jan. 18, 2011).*
http://www.stal.com.cn/pdffile/410420425440a.pdf (May 21, 2003).*
U.S. Appl. No. 09/798,749, filed Mar. 2, 2001, Multilayer medical device.

* cited by examiner

*Primary Examiner* — Max Hindenburg
*Assistant Examiner* — Jonathan M Foreman
(74) *Attorney, Agent, or Firm* — Seager Tufte Wickem LLC

(57) ABSTRACT

Medical devices having one or more cutting elements are disclosed. In some embodiments, a medical device includes an elongated catheter configured to be inserted into a body, and a cutting element carried by the catheter. The cutting element has an alloy including from about 12% to about 16% by weight of chromium, from about 0.5% to about 5% by weight of molybdenum, and iron. The alloy has a martensitic phase.

8 Claims, 3 Drawing Sheets

MEDICAL DEVICES WITH CUTTING ELEMENTS

TECHNICAL FIELD

The invention relates to medical devices, such as balloon catheters, having one or more cutting elements.

BACKGROUND

Balloon catheters can be used for a variety of medical procedures such as, for example, to widen a body vessel occluded by a tumor or restricted by plaque (as in angioplasty), to position a medical device (such as a stent or a graft), or to selectively block a passageway. A balloon catheter may include an inflatable and deflatable balloon positioned on a long and narrow catheter body. Initially, the balloon is folded around the catheter body to reduce the radial profile of the balloon for easy insertion into the body.

During use, for example, in angioplasty, the folded balloon can be positioned at a location in a vessel occluded by a stenosis by threading the balloon catheter through a guide wire emplaced in the body. The balloon is then inflated, e.g., by introducing a fluid into the interior of the balloon. Inflating the balloon can radially expand the stenosis so that the vessel can permit an increased rate of blood flow. After use, the balloon is deflated and withdrawn from the body.

In some cases, it is desirable to use a balloon catheter carrying one or more cutting elements to incise at least a portion of the stenosis. Incising the stenosis can further widen the body vessel and increase the rate of blood flow.

SUMMARY

The invention relates to medical devices including one or more cutting elements, or atherotomes.

In one aspect, the invention features a medical device including an elongated catheter configured to be inserted into a body, and a cutting element carried by the catheter. The cutting element includes an alloy comprising from about 12% to about 16% by weight of chromium, from about 0.5% to about 5% by weight of molybdenum, and iron, the alloy having a martensitic phase.

Embodiments can include one or more of the following features. The alloy further includes from about 0.35% to about 0.65% by weight of carbon. The alloy further includes from about 0.5% to about 1.5% by weight of manganese. The alloy includes from about 76% to about 87% by weight of iron. The alloy further includes from about 0.35% to about 0.65% by weight of carbon, from about 0.5% to about 1.5% by weight of manganese, and less than or equal to about 0.5% by weight of silicon, the alloy comprising from about 69% to about 87% by weight of iron. The alloy further includes nickel and/or cobalt. The device further includes a lubricious coating on the cutting element. The device further includes an oxidized layer on the cutting element. The alloy has a hardness of from about 49 to about 55 Rockwell Hardness C. The device further includes an inflatable balloon attached to the catheter, the cutting element being carried by the balloon.

In one aspect, the invention features a medical device, including an elongated catheter configured to be inserted into a body, and a cutting element carried by the catheter. The cutting element includes an alloy having a nickel equivalent and a chromium equivalent within a first area of a Schaeffler diagram, the first area being defined by 12 equivalent chromium-zero equivalent nickel, 12 equivalent chromium-15.5 equivalent nickel, and 26 equivalent chromium-4.5 equivalent nickel, wherein a chromium equivalent is equal to % Cr+% Mo+1.5×% Si+0.5×% Nb, a nickel equivalent is equal to % Ni+30×% C+0.5×% Mn, and the alloy has a martensitic phase.

Embodiments can include one or more of the following features. The alloy includes from about 12% to about 16% by weight of chromium, from about 0.5% to about 5% by weight of molybdenum, and iron. The alloy includes from about 0.35% to about 0.65% by weight of carbon. The alloy includes from about 0.5% to about 1.5% by weight of manganese. The alloy includes from about 76% to about 87% by weight of iron. The alloy includes from about 0.35% to about 0.65% by weight of carbon, from about 0.5% to about 1.5% by weight of manganese, less than or equal to about 0.5% by weight of silicon, and from about 69% to about 87% by weight of iron. The alloy further includes nickel and/or cobalt. The device further includes a lubricious coating on the cutting element. The device further includes an oxidized layer on the cutting element. The alloy has a hardness of from about 49 to about 55 Rockwell Hardness C. The device further includes an inflatable balloon attached to the catheter, the cutting element being carried by the balloon.

Embodiments may include one or more of the following advantages. The alloy can reduce (e.g., inhibit) corrosion of the cutting elements, while providing the cutting elements with good flexibility that allow the medical device to traverse a tortuous vasculature. The alloy can be hardened. As a result, the cutting elements can hold an edge and be formed relatively sharp, which can provide well defined, regular cuts with relatively low forces. Reducing random, uncontrolled cracking can reduce inflammation, other trauma to a body vessel, and/or restenosis of the body vessel. The alloy is biocompatible.

As used herein, an alloy is a substance including a mixture of two or more metals or a metal and nonmetal intimately united, such as by being fused together or dissolving in each other when molten, and remaining fused together or dissolved in each other when solid.

All concentrations expressed herein are weight percentages.

Other aspects, features and advantages will be apparent from the description of the embodiments thereof and from the claims.

DETAILED DESCRIPTION

Figure 1A:
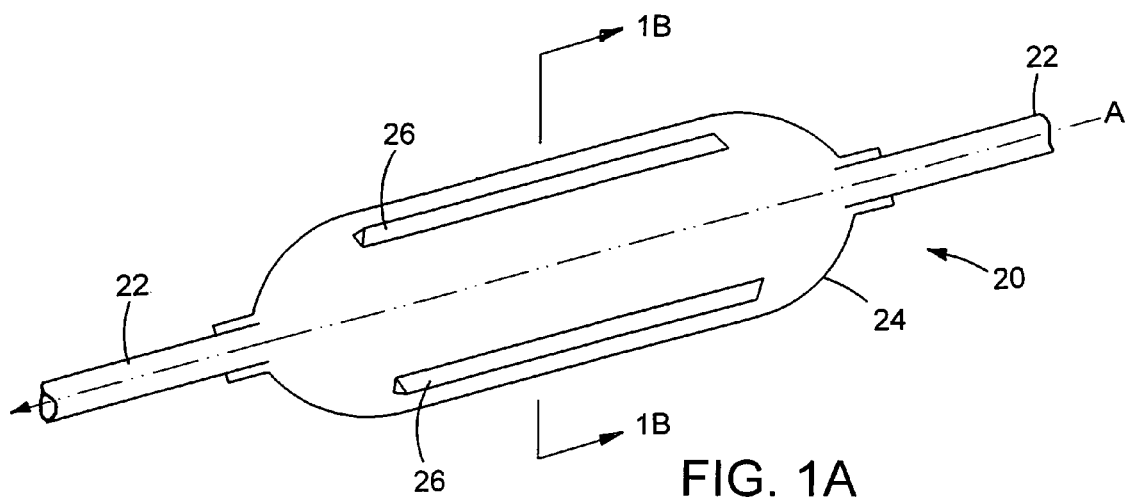
FIG. 1A is a diagrammatic view of an embodiment of a balloon catheter carrying cutting elements.
Figure 1B:
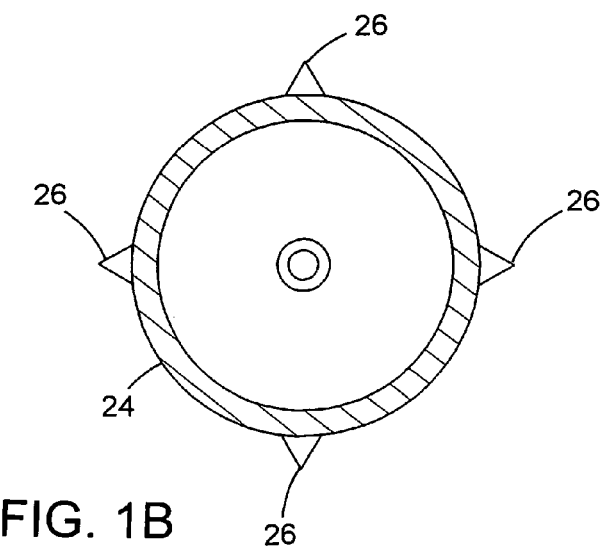
FIG. 1B is a cross-sectional view of the balloon catheter of FIG. 1A, taken along line 1B-1B.

Referring to FIGS. 1A and 1B, a balloon catheter 20 for removing stenosis, such as plaque along coronary artery walls, includes a shaft 22, an expandable balloon 24 attached to and in fluid communication with shaft 22, and one or more (as shown, four) cutting elements 26. The one or more cutting elements 26 are attached parallel to the longitudinal axis of expandable balloon 24 with a bonding material, such as, for example an adhesive or a urethane pad. The use of cutting elements 26 is by way of example only. In general, one or more scoring elements can be used. As referred to herein when carried by a medical device (e.g., balloon catheter 20), a scoring element is capable of scoring and/or cutting stenosis (e.g., plaque along artery walls). In some embodiments, a scoring element can, for example, be in the shape of a wire (e.g., a metal wire).

Figure 2:
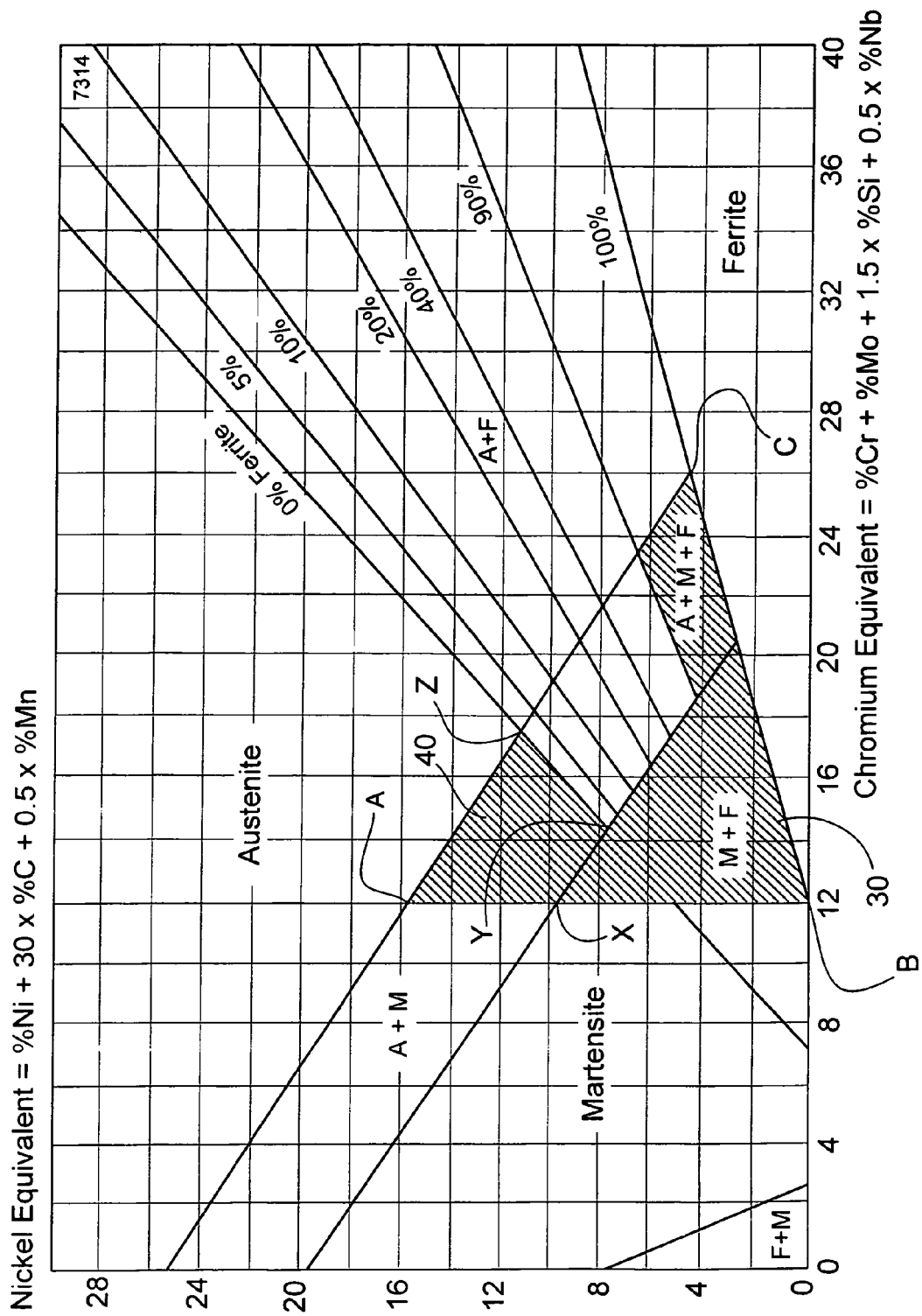
FIG. 2 is a Schaeffler diagram.

Cutting elements 26 are elongated members (e.g., blades) formed wholly or in part of a corrosion-resistant steel alloy with good flexibility. Referring to the Schaeffler diagram of FIG. 2, the alloy has a composition that falls inclusively within the shaded region 30 shown in the diagram. Without wishing to be bound by theory, it is believed that alloy compositions that fall inclusively within shaded region 30 have a balance of corrosion resistance and flexibility that enhance the performance of cutting elements 26. The alloy compositions within shaded region 30 are capable of having a fine grain microstructure that includes needle-like grains interwoven at random. It is believed that this microstructure can distribute stress evenly in many directions, thereby providing enhanced ductility and flexibility. Shaded region 30 is defined by three points: (point A) 12 equivalent chromium-15.5 equivalent nickel, (point B) 12 equivalent chromium-zero equivalent nickel, and (point C) 26 equivalent chromium-4.5 equivalent nickel. Preferred alloy compositions fall inclusively within the upper austenitic (A) and martensitic (M) trapezoidal shaded area 40, which is defined by point A and points X, Y, and Z, shown in FIG. 2. Point X is at 12 equivalent chromium-9.5 equivalent nickel; point Y is at 14.5 equivalent chromium-7.5 equivalent nickel; and point Z is at 17.5 equivalent chromium-11.0 equivalent nickel. A chromium equivalent (shown along the x-axis) is equal to, in weight percent, % Cr+% Mo+1.5×% Si+0.5×% Nb, and a nickel equivalent (shown along the y-axis) is equal to, in weight percent, % Ni+30×% C+0.5×% Mn. The alloy is synthesized and/or processed to include a fine-grained martensitic (M) phase, wholly or in part with an austenitic (A) phase and/or a ferritic (F) phase. Shaded region 30 does not include the trapezoidal area having only the austenitic phase and the ferritic phase. As described below, in some embodiments, the alloys include chromium, carbon, silicon, manganese, molybdenum, and iron. The alloys can further include cobalt and/or nickel.

Chromium can be added to the alloy to make the alloy more corrosion resistant, e.g., to improve the pitting resistance. In certain embodiments, at 12 weight percent or higher, chromium can form a thin oxide layer on the surface of a steel that enhances the resistance of the steel to corrosive attack. The degree of corrosion resistance is a function of the chromium concentration and the concentrations of other elements in the steel. But having too much chromium may form undesirable carbides because chromium is a strong carbide former. In some embodiments, the alloy includes from about 12 to about 16 weight percent of chromium. The alloy can include greater than or equal to about 12, about 12.5, about 13, about 13.5, about 14, about 14.5, about 15, or about 15.5 weight percent, and/or less than or equal to about 16, about 15.5, about 15, about 14.5, about 14, about 13.5, about 13, or about 12.5 weight percent of chromium.

Carbon can be added to the alloy to combine with iron to form the martensitic phase. But carbon can also combine with chromium and adding too much carbon can form undesirable levels of carbides. In some embodiments, the alloy includes from about 0.35 to about 0.65 weight percent of carbon. The alloy can include greater than or equal to about 0.35, about 0.40, about 0.45, about 0.50, about 0.55, or about 0.60 weight percent, and/or less than or equal to about 0.65, about 0.60, about 0.55, about 0.50, about 0.45, or about 0.40 weight percent of carbon.

Silicon can be added to the alloy to help maintain the hardness of the martensitic phase while providing good ductility. Silicon may also allow the alloy to be heat treated (e.g., tempered) at a high temperature, thereby allowing the crystal lattice to relax, to equalize stress and to decrease the risk of premature fatigue. In some embodiments, the alloy includes from about 0.05 to about 0.50 weight percent of silicon. The alloy can include greater than or equal to about 0.05, about 0.10, about 0.15, about 0.20, about 0.25, about 0.30, about 0.35, about 0.40, or about 0.45 weight percent, and/or less than or equal to 0.50, about 0.45, or about 0.40, about 0.35, about 0.30, about 0.25, about 0.20, about 0.15, or about 0.10 weight percent of silicon.

Manganese can be added to the alloy to help keep the microstructure of the alloy martensitic and to reduce coalescence of carbides. In some embodiments, the alloy includes from about 0.50 to about 1.5 weight percent of manganese. The alloy can include greater than or equal to about 0.50, about 0.60, about 0.70, about 0.80, about 0.90, about 1.0, about 1.1, about 1.2, about 1.3, or about 1.4 weight percent, and/or less than or equal to about 1.5, about 1.4, about 1.3, about 1.2, about 1.1, about 1.0, about 0.9, about 0.8, about 0.7, or about 0.60 weight percent of manganese.

Molybdenum can be added to the alloy to enhance the resistance of the alloy to corrosion, e.g., pitting and crevice corrosion. Molybdenum can also serve as a grain refiner and enhance the hardness of the alloy. In some embodiments, the alloy includes from about 0.05 to about 5.0 weight percent of molybdenum. The alloy can include greater than or equal to about 0.05, about 0.50, about 1.0, about 1.5, about 2.0, about 2.5, about 3.0, about 3.5, about 4.0, or about 4.5 weight percent, and/or less than or equal to about 5.0, about 4.5, about 4.0, about 3.5, about 3.0, about 2.5, about 2.0, about 1.5, about 1.0, or about 0.5 weight percent of molybdenum.

The alloy can further include cobalt and/or nickel. Cobalt may be added, for example, to increase wear resistance, and nickel may be added, for example, to enhance toughness. In some embodiments, the alloy includes from about 0.5 to about 1.5 weight percent of cobalt (e.g., greater than or equal to about 0.5 or about 1.0 weight percent; and/or less than or equal to about 1.5 or 1.0 weight percent). In some embodiments, the alloy includes from about 1.0 to about 5.0 weight percent of nickel. The alloy can include greater than or equal to about 1.0, about 2.0, about 3.0, or about 4.0 weight percent of nickel; and/or less than or equal to about 5.0, about 4.0, about 3.0, or about 2.0 weight percent of nickel.

Iron makes up the balance of the alloy, e.g., after accounting for the other elements in the alloy described above. In certain embodiments, the alloy includes from about 69 (e.g., 69.85) to about 87 (e.g., 87.05) weight percent of iron. The alloy can include greater than or equal to about 69, about 71, about 73, about 75, about 77, about 79, about 81, about 83, or about 85 weight percent of iron; and/or less than or equal to about 87, about 85, about 83, about 81, about 79, about 77, about 75, about 73, or about 71 weight percent of iron.

The alloy can be made by combining the elemental components in the selected concentration, and forming an intimate and homogeneous composition. For example, the targeted alloy can be formed by melting charges of elemental starting materials (such as chips, powders, balls, pellets, bars, wires, and/or rods) in the concentrations described above. Melting can be performed in an inert atmosphere (e.g., argon pressure), in a partial pressure (in argon at a pressure less than atmospheric) or under vacuum using vacuum induction melting (VIM), vacuum arc remelting (VAR), electron beam melting (EBM), plasma melting, vacuum or inert gas plasma deposition, hot isostatic pressing, and/or cold pressing and sintering. The raw samples (initial form of the alloy) can be in the form of an ingot, a compact, or a deposit. An example of the alloy is also available commercially under Chrome-Flex 7C27M02 (from Sandvik Bioline), which includes about 0.38% carbon, 0.40% silicon, 0.55% manganese, about 1% molybdenum, about 13.5% chromium, and a balance of iron.

To form cutting elements from the raw samples, techniques such as, for example, wire electrical discharge machining (EDM), laser machining, grinding, punching, scoring and chemical etching, can be used. The alloy can be processed to provide a desired hardness, for example, by heat treating at about 926° C. to about 1066° C. for 0.5-1.0 hour, or until the alloy has a hardness of from about 49 to about 55 on the Rockwell Hardness C scale. As an example, the raw material can be purchased from a manufacturer in a continuous strip and in the annealed condition, and subsequently processed into microtomes or cutting blades (e.g., by Crescent Specialty Blades, Fremont, Ohio). Processing may include punching and scoring the strip and heat treating to obtain the desired hardness. After heat treatment, the strip may be processed through a strip grinder to sharpen, hone and strop a cutting edge on one edge of the strip. At the end of the strip grinding process, the strip can be sheared into desired lengths of microtomes. The microtomes can be processed using fine wire EDM to fabricate atherotomes, which may then be cleaned prior to casting a pad (e.g., a urethane pad) onto the base of the atherotome.

Cutting elements 26 are generally configured to be carried by a medical device, such as a balloon catheter, and to be insertable into the body. In some embodiments, cutting elements 26 have a length of about 6 to about 40 mm. The height of cutting elements can range from about 0.27 to about 0.84 mm.

Expressed another way, cutting elements 26 may be sized to be carried by expandable balloon 24, which can have any of a variety of shapes or sizes. In certain embodiments, expandable balloon 24 can be a coronary balloon, an aortic balloon, a peripheral balloon, a reperfusion balloon, an endoscopy balloon, a gastrointestinal balloon, a urological balloon or a neurological balloon. In some embodiments, balloon 24 has a diameter of at least one millimeter (e.g., at least about two millimeters, at least about three millimeters, at least about four millimeters, at least about five millimeters, at least about six millimeters) when inflated. As an example, balloon 24 can be a peripheral balloon having a diameter of at least about three millimeters (e.g., at least about five millimeters, at least about seven millimeters, at least about nine millimeters, at least about 12 millimeters) when inflated. As another example, balloon 24 can be a urological balloon having a diameter at least about four millimeters (e.g., at least about 10 millimeters, at least about 20 millimeters, at least about 30 millimeters, at least about 40 millimeters) when inflated. As a further example, balloon 24 can be a neurological balloon having a diameter at least about 1.5 millimeters (e.g., at least about two millimeters, at least about three millimeters, at least about four millimeters, at least about five millimeters).

A variety of embodiments of balloon catheters can be used. Examples of balloon catheter 20 are described in, for example, Wang U.S. Pat. No. 5,195,969, and Hamlin U.S. Pat. No. 5,270,086, both hereby incorporated by reference; and are exemplified by the Express® or Maverick® systems available from Boston Scientific Corp., Maple (hove, MN. In some cases, balloon 24 is a non-elastic balloon, e.g., a non-distendable balloon made of, e.g., PET. Balloon 24 can include one or more biaxially-oriented layers. In other embodiments, balloon 24 and/or catheter body 22 can have a wall having a plurality of layers formed of polymers. Multilayer devices are described in Hamlin U.S. Pat. No. 5,270,086; Wang U.S. Pat. No. 5,195,969; Hamilton U.S. Pat. No. 5,797,877; and U.S. Ser. No. 09/798,749, entitled "Multilayer Medical Device" and filed on Mar. 2, 2001 and published on Nov. 2, 2002 as U.S. Publication No. 20020165523, all hereby incorporated by reference in their entirety. The layers can be selected to provide catheter body 22 and/or balloon 24 with desired properties. Different combinations of layering, e.g., materials, sequence, and/or thickness, can be used, as described in U.S. Ser. No. 09/798,749. Other embodiments of balloons, e.g., with discrete longitudinal stripes, are described in US-2003-0163148-A1.

Balloon 24 can be folded using the methods described in Vigil U.S. Pat. Nos. 5,209,799 and 5,336,234, both hereby incorporated by reference in their entirety. In certain embodiments, relatively compliant areas of balloon 24, e.g., flaps, can be folded over cutting elements 26 to protect a patient's body lumen from cutting elements 26. Folding can be performed by engaging, e.g., grasping, the flaps with a chuck, and rotating the chuck. Folding can be performed during heat treatment of balloon 24, as described in Vigil U.S. Pat. No. 5,209,799. Other methods of folding balloon 24 are described in U.S. Ser. No. 10/087,303 filed on Feb. 28, 2002 and published on Aug. 28, 2003 as U.S. Publication No. 2003163157.

Figure 3A:
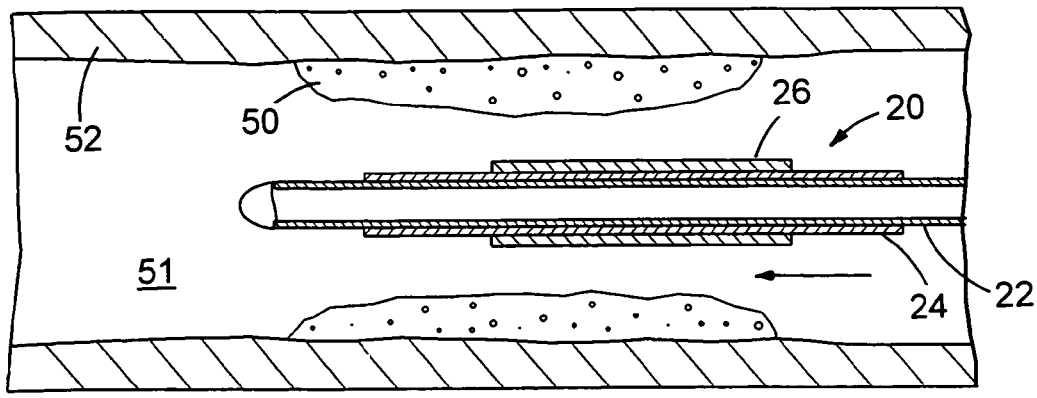
FIGS. 3A, 3B, and 3C are diagrammatic views of an embodiment of a method of using a balloon catheter.
Figure 3B:
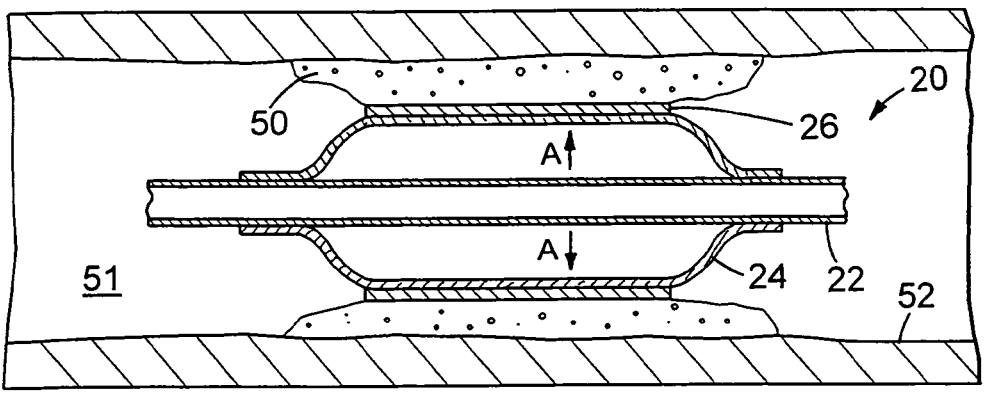
Figure 3C:
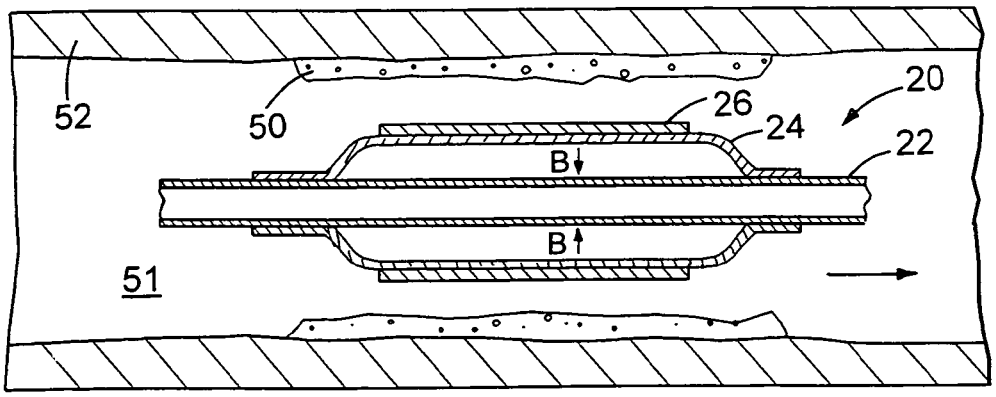

Referring to FIGS. 3A, 3B, and 3C, a method of using catheter 20 is shown. Catheter 20 is delivered to a target site 51, e.g., one having a calcified region 50, using conventional methods such as by passing catheter shaft 22 over an emplaced guide wire (not shown). Balloon 24 is unexpanded so that catheter 20 can easily navigate through the patient's body without causing trauma to vessel walls 52. After catheter 20 is properly positioned, expandable balloon 24 is radially expanded (arrows A shown in FIG. 3B), e.g., by introducing a fluid into the interior of the balloon through an inflation lumen (not shown) extending along catheter shaft 22. As expandable balloon 24 is expanded, the one or more cutting elements 26 are advanced radially outward toward calcified region 50 until cutting elements 26 pierce and/or contact calcified region 50. Catheter 20 can be moved (e.g. translated and/or rotated) to provide a desired cutting action to remove, at least in part, calcified region 50 from vessel wall 52. Subsequently, expandable balloon 24 is deflated (arrows B shown in FIG. 3C) so that cutting elements 26 are withdrawn from the vessel wall 52. Catheter 20 is then removed according to conventional methods.

In general, catheter 20 can be used to treat blocked or partially blocked lumens within a patient's body. For example, in certain embodiments, catheter 20 is used to treat blockages in coronary arteries. In some embodiments, catheter 20 is used to treat blockages in the urinary tract. In certain embodiments, catheter 20 is used to treat blockages in the gastrointestinal tract.

While certain embodiments have been described, other embodiments are also possible.

For example, in some embodiments, one or more of cutting elements 26 includes a lubricious coating to help the cutting elements pass through a vessel. The coating can be hydrophilic (e.g., a Bioslide™ coating) or hydrophobic (e.g., MDX)

Cutting elements 26 can be carried by a catheter, for example, by attaching the cutting elements directly or indirectly to the balloon. For example, cutting elements 26 can be attached to a balloon by a pad, as described in commonly assigned U.S. Ser. No. 10/744,507, filed Dec. 22, 2003, and published on Jul. 7, 2005, as U.S. Publication No.

200500149102. An adhesion promoter (such as a silane) may be applied to the surfaces of cutting elements 26 to strengthen the bond to the balloon.

In some embodiments, exposed surfaces of cutting elements 26 are passivated to further enhance corrosion resistance. For example, the surfaces of cutting elements 26 can be oxidized by treating the cutting elements with nitric acid or citric acid. Alternatively or additionally, the surfaces can be further hardened by coating with materials such as titanium nitride and nickel-containing polytetrafluoroethylene.

In addition to balloon catheters, cutting elements 26 can be carried by other types of catheters, such as ablation catheters, e.g., radiofrequency ablation catheters and laser ablation catheters.

While catheter 20 is shown having four cutting elements 26, in other embodiments, the catheter can have one, two, three, five, six, seven, eight, or more cutting elements. Cutting elements 26 can be equally and/or unequally spaced around the circumference of balloon 24. For example, looking at a radial cross section (e.g., FIG. 2) of a balloon having six cutting elements 26, the cutting elements can be formed at 2 o'clock, 3 o'clock, 4 o'clock, 8 o'clock, 9 o'clock, and 10 o'clock. Cutting element 26 at 3 o'clock is equally spaced from the cutting elements at 3 o'clock and 4 o'clock; but, for example, the cutting element at 4 o'clock is unequally spaced from the cutting elements at 3 o'clock and 8 o'clock. Cutting elements 26 can be symmetrically or asymmetrically positioned around the circumference of balloon 24.

Multiple cutting elements 26, e.g., two, three, four, five, six, or more, can be arranged collinearly (e.g., spaced and end-to-end) along balloon 24, which can enhance the flexibility of the balloon. Multiple cutting elements 26 can be arranged side-by-side, e.g., adjacent to each other. Multiple cutting elements 26 can be arranged adjacent to each other and overlapping along the longitudinal direction of balloon 24. A balloon can have one or more sets of cutting elements arranged as described above.

All publications, references, applications, and patents referenced in this application are herein incorporated by reference in their entirety.

Other embodiments are within the claims.

What is claimed is:

1. A medical device, comprising:
   an elongated catheter configured to be inserted into a body;
   an inflatable balloon attached to the catheter; and
   a cutting element carried by the balloon, the cutting element comprising an alloy having a nickel equivalent and a chromium equivalent within a first area of a Schaeffler diagram, the first area being defined by 12 equivalent chromium-zero equivalent nickel, 12 equivalent chromium-15.5 equivalent nickel, and 26 equivalent chromium-4.5 equivalent nickel,
   wherein a chromium equivalent is equal to % Cr+% Mo+1.5×% Si+0.5×% Nb, a nickel equivalent is equal to % Ni+30×% C+0.5×% Mn, and the alloy comprising at least two phases, one of the phases being a martensitic phase;
   wherein the alloy comprises from about 0.35% to about 0.65% by weight of carbon;
   wherein the alloy comprises from about 12% to about 16% by weight of chromium, from about 0.5% to about 5% by weight of molybdenum, and iron.

2. The device of claim 1, wherein the alloy comprises from about 0.5% to about 1.5% by weight of manganese.

3. The device of claim 1, wherein the alloy comprises from about 76% to about 87% by weight of iron.

4. The device of claim 1, wherein the alloy comprises from about 0.5% to about 1.5% by weight of manganese, less than or equal to about 0.5% by weight of silicon, and from about 69% to about 87% by weight of iron.

5. The device of claim 4, wherein the alloy further comprises nickel and/or cobalt.

6. The device of claim 1, further comprising a lubricious coating on the cutting element.

7. The device of claim 1, further comprising an oxidized layer on the cutting element.

8. The device of claim 1, wherein the alloy has a hardness of from about 49 to about 55 Rockwell Hardness C.

* * * * *

UNITED STATES PATENT AND TRADEMARK OFFICE
CERTIFICATE OF CORRECTION

| | |
|---|---|
| PATENT NO. | : 8,052,703 B2 |
| APPLICATION NO. | : 11/169415 |
| DATED | : November 8, 2011 |
| INVENTOR(S) | : St. Martin et al. |

It is certified that error appears in the above-identified patent and that said Letters Patent is hereby corrected as shown below:

Column 5
Line 62, delete "(hove", and insert therefore -- Grove --.

Signed and Sealed this
Third Day of January, 2012

David J. Kappos
*Director of the United States Patent and Trademark Office*